United States Patent [19]

Comby

[11] Patent Number: 4,654,556
[45] Date of Patent: Mar. 31, 1987

[54] APPARATUS FOR EXAMINING SAMPLES BY ELECTRON EMISSION

[75] Inventor: Georges Comby, Humbert, France

[73] Assignee: Commissariat A l'Energie Atomique, Paris, France

[21] Appl. No.: 541,130

[22] Filed: Oct. 12, 1983

[30] Foreign Application Priority Data

Oct. 19, 1982 [FR] France ................. 82 17472

[51] Int. Cl.$^4$ ......................... H01J 47/00; G21K 5/10
[52] U.S. Cl. ..................................... 313/93; 250/442.1
[58] Field of Search ................. 313/93, 309; 250/385, 250/306, 307, 282, 285, 288, 289, 441.1, 442.1

[56] References Cited

U.S. PATENT DOCUMENTS

| 2,692,948 | 10/1954 | Lion | 313/93 X |
|---|---|---|---|
| 3,852,595 | 12/1974 | Aherth | 313/309 X |
| 4,033,904 | 7/1977 | Gerlach et al. | 250/442.1 |
| 4,280,075 | 7/1981 | Comby et al. | 313/93 |
| 4,486,659 | 12/1984 | Turner | 250/306 |

FOREIGN PATENT DOCUMENTS 0007842 2/1980 European Pat. Off. .

OTHER PUBLICATIONS

"Le Vide", vol. 35, No. 203, Sep./Oct. 1980.
"Metallurgical Transactions", vol. 8A, Jun. 1977.

Primary Examiner—Palmer C. DeMeo
Assistant Examiner—Sandra L. O'Shea
Attorney, Agent, or Firm—Pearne, Gordon, McCoy & Granger

[57] ABSTRACT

The invention relates to the examination of samples which, by thermal or photon excitation, are able to emit electrons. These electrons are detected and located by a counter incorporating a cathode forming a mesh network. Pointed anodes coincide with the axes of the meshes. The enclosure of the apparatus is sealed by the sample and its excitation means. The invention can be used in dosimetry or in the checking of surface states.

10 Claims, 2 Drawing Figures

APPARATUS FOR EXAMINING SAMPLES BY ELECTRON EMISSION

BACKGROUND OF THE INVENTION

The present invention relates to the examination of samples able to emit electrons, particularly as a result of a stimulation, caused by an in particular thermal or photon excitation with a view to detecting and locating these electrons.

A first application of this type of examination uses certain sample materials, which, during thermal stimulation, emit an electron flow which can be used for measuring the intensity of a specific excitation previously undergone by the sample. These sample materials are lag time converters of phenomena which it is wished to observe. For example, this first application relates to the examination of converter materials also used more particularly as radiation dosimeters used for the protection of personnel working in areas liable to be irradiated.

Hitherto, these thermostimulated electrons have been detected and located, either with the aid of electron multipliers requiring a high quality vacuum, or by integration in an ionization chamber, or by the use of electron multiplication counters in gases. These different protection processes use precise equipment, which are very difficult, sensitive and therefore costly to manufacture. In addition, they do not make it possible to analyse samples having a large surface, or to simply detect in a separate manner the exoelectrons emitted by several specialized areas of the converter material.

A second application of this type of examination is the location of surface defects. Hitherto, for obtaining information on the structure, homogeneity, composition, etc of surfaces, various methods have been used ranging from optical microscopy with X-ray diffraction, to ultrasonic analysis or scanning electron microscopy. However, these highly technical methods are unsuitable for detecting insipient microcracks, which can be clearly revealed by photon excitation, which causes electron emission.

Thus, the crystalline modifications of materials subject to various stresses are accompanied by dislocations which, on a macroscopic scale, act as electron traps and very locally disturb the Fermi level of the material. Optical stimulation which can be applied in a local and detectable manner releases part of these electrons, thus revealing the presence, at a precise location, of surface defects.

SUMMARY OF THE INVENTION

The object of the present invention is to propose an apparatus for examining samples by electron emission and in particular stimulated, which is simple, does not require operation under vacuum, robust, able to conveniently examine samples no matter what their dimensions, permits a separate analysis of the different areas of the sample and forms an apparatus which can be used in an industrial medium and not only in the laboratory.

To this end, the invention consists of applying in a novel manner part of a known "apparatus for the detection and location of radiation", forming the object of French Patent No. 78 20807, filed on July 12th 1978, in the name of the present Applicant.

This existing patent relates to an apparatus for the detection and location of radiation comprising in a tight enclosure a cathode, a plurality of filamentary anodes insulated from one another and polarized with respect to the cathode and photosensitive means, the tight enclosure being provided with a shielding window which is transparent to the radiation in question facing the cathode and anodes, wherein it comprises an insulating support having two faces and whereby part of one face, which faces the shielding window, is coated with a conductive material forming a mesh network constituting the cathode, the ends of the anodes being pointed and the axes of the anodes coinciding respectively with the axes of the mesh network, said points being set back relative to the face of the insulating support coated with the network of conductive meshes.

Reference should be made to the text and drawings of this earlier patent to obtain a better understanding of the structure and operation of this radiation detection and location apparatus.

The originality of this apparatus results from the fact that it is formed from a matrix of independent cells, although there is no material insulation between these cells. This results from the shape of the matrix cathode and the position of the pointed anodes below said matrix and at this level, the insulating support permits a material optical insulation between the multiplying zones of the points and between said zones and the cathode. The appropriate control of the potentials applied to the different components of the detector makes it possible to create electric field lines permitting said functional independence of the cells. The existence of an equipotential conducting pattern in front of the shielding window imposes a precise configuration of the field lines, so that it constitutes a drift space and also ensures the neutralization of the positive charges produced during the multiplications.

This originality leads to the appearance within the detector of two contiguous, complementary zones, linked with the detection phenomenon of the emitted electrons. Moreover, there is an electron drift space in the area located beyond the matrix cathode with respect to the pointed anodes and said drift space is also subdivided into independent cells, so that an electron generated and detached in a cell of the drift space will remain therein, permitting an unambiguous location. Moreover, around each anodic point, there is formed an intense electron multiplicaton zone, which makes it possible to reveal a single primary electron and which supplies on the pointed anodes pulses of high amplitudes and which vary little as a function of the electron position relative to the anode.

The invention consists of utilizing these features and performances of a cathode focusing multipoint detector in order to form an apparatus for examining samples by stimulated electron emission.

The present invention therefore specifically relates to an apparatus for the examination of samples by electron emission, wherein it comprises in an enclosure an insulating support, whereof part of one face is coated with a conductive material forming a network of meshes constituting a cathode, a plurality of anodes insulated from one another and polarized with respect to the cathode and being in the form of points, whose axes respectively coincide with the axes of the meshes of the cathode network, said points being set back with respect to the face of the insulating support coated with the conductive mesh network, said enclosure having an opening positioned beyond the anodes with respect to the matrix cathode, said opening serving to house the samples to be examined, the apparatus also having means for making the interior of the enclosure tightly sealed, means for filling the tight interior of the enclosure with a multiplying gaseous medium and means for applying an excitation to the sample.

Generally, the known apparatus for the examination of samples by electron emission comprise electrodes located in a tight enclosure containing the sample, this enclosure being closed by a shielding window covered by a conductive pattern. In accordance with the invention, the sample is substituted for the shielding window and an associated cathode mesh and point anode counter catches substantially all the electrons emitted by the surface of the sample.

According to a first application of the invention, the sample examination apparatus is characterized in that the sample excitation means are thermal excitation means.

According to a second application of the invention, the sample examination apparatus is characterized in that the said excitation means are photon excitation means.

According to a special feature, means are provided for filling the tight interior of the enclosure with methane under atmospheric pressure.

According to another special feature, the sample examination apparatus has means for carrying out and controlling relative displacements of the apparatus with respect to the sample.

According to yet another special feature, the sample occupying the recess makes the interior of the enclosure tightly sealed.

BRIEF DESCRIPTION OF THE DRAWINGS

Two embodiments of the invention will be described in non-limitative manner hereinafter relative to the drawings, wherein show.

DETAILED DESCRIPTION OF THE INVENTION

Figure 1:
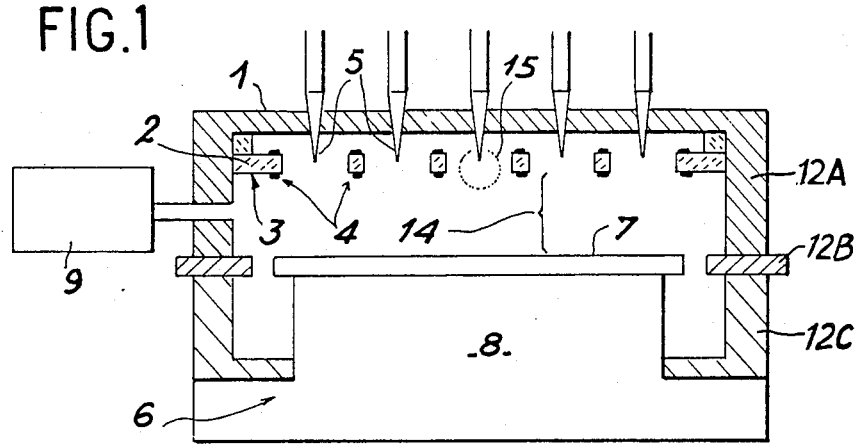
FIG. 1 diagrammatically and in section, an apparatus according to the invention for the detection of thermoexoelectrons.

Reference is firstly made to FIG. 1, which diagrammatically shows an apparatus for the examination of thermoexcitable samples with a view to emitting electrons. The apparatus has, within an enclosure 1, a cathode formed by an insulating support 2, whereof part of the face 3 is coated with a coating 4 of a conductive material forming a network of meshes constituting the cathode.

A plurality of insulated anodes 5 in the form of points and their axes respectively coincide with the axes of the meshes of cathode network 4. These pointed anodes 5 are set back relative to the cathode network 4.

The enclosure has an opening 6 on its face beyond anodes 5 with respect to cathode 4. In opening 6 is located the thermoexcitable sample 7, which is more specifically carried by a thermostimulation element 8. The interior of enclosure 1 is tight, when the sample is in the examination position, as shown in FIG. 1.

A source 9 of multiplying gas, e.g. methane under atmospheric pressure is provided for filling the tight interior of enclosure 1. It should be noted that on placing in the examination apparatus, a sample formed from juxtaposed areas of different sensitivities to irradiation, the signs representing the excitations undergone by these different areas could be taken on groups of different anodes corresponding to these different areas.

The fluidtight enclosure 1 is formed by assembly of the body 12A with the elements 8, and 12C as shown. The fluidtight sealing of such elements relative to each other is accomplished by conventional seal means 12B.

Figure 2:
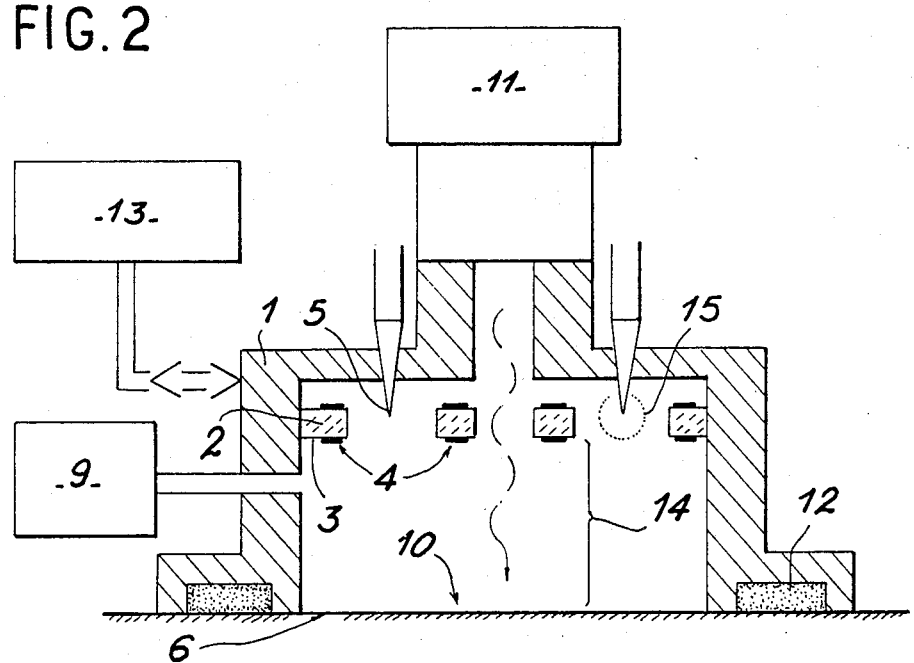
FIG. 2 diagrammatically and in section, an apparatus according to the invention for locating surface defects.

FIG. 2 diagrammatically shows an apparatus for the examination of photoexcitable samples with a view to emitting electrons. The same reference numerals are used as in FIG. 1 for identical elements, which will not be described again.

In this case, the sample is constituted by a surface 10 to be scanned. An optical light source 11 makes it possible to excite this surface. A sealing member 12 is placed between the base of enclosure 1 and surface 10. An apparatus 13 makes it possible to define the relative position of the mobile examination apparatus with respect to the surface to be scanned.

In FIGS. 1 and 2, it is possible to see the drift space 14 of the electrons referred to hereinbefore, as well as the areas 15 for electron multiplication in a gaseous medium.

In all cases, it is advantageous to have an auxiliary electrode like that of the earlier-dated patent on the face of the insulating support opposite to that carrying the cathode.

It is obvious that the special conditions of applying the invention will be chosen as a function of the envisaged aims. The parameters such as the intensity and performance in time of the thermal or photon excitations will be chosen in an appropriate way, together with the values of the potentials applied to the various electrodes.

It has been indicated hereinbefore that the sample occupies the location of the observation shielding window of the radiation detection and location apparatus of the aforementioned patent. Thus, its surface is necessarily conductive, in order to constitute an equipotential which can be likened to the conductive pattern described in the aforementioned patent. In the case where the sample is insulating, it is indispensable to utilize a known procedure for producing this equipotential. For example, it is possible to mix a sample in divided form with a conductive material, or a conductive pattern can be deposited on the sample, etc.

The above description is only given in exemplified manner and other realisations can easily be envisaged. Moreover, it is possible to envisage applications of the invention in which the sample stimulation means are not thermal or photon, even applications where there is in fact no stimulation means, the electrons appearing spontaneously on the surface of a sample, e.g. during the process for the decay of exoemissions due to triboexcitation.

What is claimed is:

1. An apparatus for the examination of solid sample by stimulated electron emission, which comprises:
   an enclosure;
   an insulating support located within the enclosure and having at least one face, at least a part of the face being coated with a conductive material to form a network of meshes, the meshes defining a first set of axes and the network of meshes comprising a cathode;
   a plurality of anodes located within the enclosure and being insulated from one another and polarized with respect to the cathode, the anodes further being in the form of points, the points defining a second set of axes, the second set of axes coinciding with the first set of axes and the points being set back with respect to the conductive mesh network;

the enclosure defining an opening positioned beyond the anodes with respect to the conductive mesh network, the opening serving to house said sample;

a closure member which comprises said sample which closes said enclosure and with sealing means interacting with said enclosure to form a tight seal;

filling means for filling the enclosure with a multiplying gaseous medium; and excitation means to apply an excitation to the sample.

2. An apparatus according to claim 1, wherein the sample excitation means are thermal excitation means.

3. An apparatus according to claim 1, wherein the sample excitation means are photon excitation means.

4. An apparatus according to one of the claims 1 to 3, wherein means are provided for filling the tight interior of the enclosure with multiplier gas under atmospheric pressure.

5. An apparatus according to claim 4, wherein the multiplier gas is methane.

6. An apparatus according to claim 1, further comprising means for carrying out and checking the relative displacements of the apparatus with respect to the sample.

7. An apparatus according to claim 3, wherein the photon excitation means are constituted by a tight source integral with the enclosure and supplying a beam of light located through an opening in the enclosure and a corresponding opening of the insulating support.

8. An apparatus according to claim 7, wherein the cathode and the anodes are arranged symmetrically around the light beam axis.

9. An apparatus as set forth in claim 1, wherein said closure member is comprised of the sample.

10. An apparatus as set forth in claim 2, wherein the sample engages the thermal excitation means and the closure member is comprised of the sample and the thermal excitation means.

* * * * *

UNITED STATES PATENT AND TRADEMARK OFFICE
CERTIFICATE OF CORRECTION

PATENT NO. : 4,654,556

DATED : March 31, 1987

INVENTOR(S) : Georges Comby

It is certified that error appears in the above-identified patent and that said Letters Patent is hereby corrected as shown below:

Column 6, line 8, claim 7, change "tight" to --light--.

Signed and Sealed this

Sixth Day of October, 1987

Attest:

Attesting Officer

DONALD J. QUIGG

Commissioner of Patents and Trademarks